United States Patent [19]

Murty

[11] 4,180,465

[45] Dec. 25, 1979

[54] FLUID COLLECTION DEVICE WITH PHASE SEPARATION MEANS

[75] Inventor: Vabilisetti S. Murty, Creve Coeur, Mo.

[73] Assignee: Sherwood Medical Industries Inc., St. Louis, Mo.

[21] Appl. No.: 642,514

[22] Filed: Dec. 19, 1975

[51] Int. Cl.² ............................................ B01D 21/26
[52] U.S. Cl. ........................... 210/516; 210/DIG. 23; 233/1 A
[58] Field of Search .................... 23/258.5, 230 B, 259, 23/292; 106/287 SB; 210/65, 83, 84, 512, 511, 515, DIG. 23, 514, 513; 233/1 A, 1 R, 26; 128/214 R, 2 F, DIG. 5

[56] References Cited

U.S. PATENT DOCUMENTS

| | | | |
|---|---|---|---|
| 3,437,266 | 4/1969 | Patterson | 210/DIG. 24 |
| 3,519,400 | 7/1970 | Anderson | 210/DIG. 24 |
| 3,647,070 | 3/1972 | Adler | 210/DIG. 24 |
| 3,852,194 | 12/1974 | Zine | 210/83 |
| 3,920,549 | 11/1975 | Gigiello et al. | 210/83 |
| 4,021,340 | 5/1977 | Zine | 210/515 |

Primary Examiner—Frank Sever
Attorney, Agent, or Firm—Stanley N. Garber; William R. O'Meara

[57] ABSTRACT

A fluid collection device includes a blood collection tube having a negative pressure therein and sealed at one end by a stopper pierceable by a needle cannula for drawing a blood specimen into the tube for centrifugal separation into a relatively light phase, plasma or serum, and a relatively heavy phase including the blood cells. A quantity of a gel-like mixture of liquid hydrocarbon-polymer, such as polybutene, and an inorganic powder, such as silica powder, is disposed in the tube. The gel-like mixture has a specific gravity intermediate those of the relatively light and heavy phases of the blood so that during centrifugation, the gel-like mixture moves to a position between the phases to provide a partition barrier between them.

19 Claims, 5 Drawing Figures

FLUID COLLECTION DEVICE WITH PHASE SEPARATION MEANS

BACKGROUND OF THE INVENTION

This invention relates to fluid collection devices and more particularly to fluid collection devices such as blood collection devices having blood phase partitioning means.

In taking blood samples for clinical testing, for example, it is common practice to employ an air evacuated blood collection tube and a needle holder having a double-ended needle cannula for drawing the blood sample. After the distal end of the needle is inserted into a body vessel, such as a vein, the tube stopper is pierced by the proximal end of the needle so that whole blood is drawn into the tube by the negative pressure. Where it is desired to analyze the serum or the plasma component of the blood, the tube is placed in a centrifuge where the lighter phase, serum or plasma, is centrifugally separated from the heavier phase which includes the blood cells. As is well known, when serum is to be separated, the whole blood is allowed to clot so that upon centrifugal separation, the lighter phase is serum. When plasma is to be tested, an anticoagulant is used with the blood to prevent clotting so that the centrifugally separated lighter phase is plasma.

Various devices have been used to isolate the separated phases from each other. For example, the collection tube may be carefully opened after separation and the lighter phase removed such as by carefully siphoning it, or a separating device may be inserted through the light phase and positioned at the interface or between the phases so that the lighter phase only can be poured from the tube. These methods and devices have the disadvantages of being relatively complicated in operation, time consuming, and they present the possibility that the specimen will be contaminated or that personnel will be exposed to a disease-carrying specimen.

In U.S. Pat. No. 3,780,935, a collection tube is opened before centrifugation and a dispenser containing a sealant of silicone fluid and silica is inserted in the open end of the blood filled tube. The sealant has a specific gravity intermediate the specific gravity values of the two phases and is released from the device by centrifugal forces during centrifugation. The sealant moves to a position between the two phases to provide a partition or barrier between the phases. This method has the undesirable feature that the collection tube must be opened by personnel in order to insert the dispenser. Also, silicone fluid based sealants have produced oil-like films or "droplets" in the lighter phase causing the clogging or tubing, especially when using automated chemistry or blood analyzers.

U.S. Pat. No. 3,852,194 discloses the use of a gel-like material such as silicone fluid and a filler which is disposed in the collection tube before the collection tube is used to draw blood from the patient. This material has a specific gravity intermediate the specific gravities of the separated phases so that it forms a barrier between the separated phases. This patent also gives examples of various oils that may be used. While this reference discloses an arrangement whereby the phases are isolated without opening the collection tube, there is generally the problem of oil from the silicone gel-like material causing clogging of tubing in the testing equipment, as mentioned above.

In U.S. Pat. No. 3,909,419, a plurality of micro encapsulated beads of gelatin are disposed between a pair of cylinders with these elements having specific gravities related such that, after the phases have been separated, the speed of the centrifuge can be increased to cause the cylinders to move toward each other to rupture the beads so that the gelatin forms a seal between the two phases. This device requires the relatively expensive manufacture of encapsulated beads, and necessitates centrifugation at two different speeds.

Various other types of centrifugally actuated phase separators have been proposed. Some include relatively complicated valves, filters or pistons, and some require relatively expensive collection tubes having a removable closure at each end in order to enable the device to be operable for both serum and plasma.

SUMMARY OF THE INVENTION

It is therefore an object of the present invention to provide a fluid collection device with means for partitioning a relatively light phase from a relatively heavy phase of fluid which avoids the above undesirable features.

More specifically, it is an object of the present invention to provide a blood collection device having improved means for maintaining the light and heavy phases of blood separated, which is relatively simple and economical, and which can be used for serum or plasma separation without requiring a tube openable at both ends.

In accordance with the present invention, a fluid collection container, for receiving a fluid adapted to be centrifugally separated into relatively light and heavy phases, is provided with a gel-like material including a liquid hydrocarbon-polymer. The material is flowable during centrifugation and has a specific gravity between the specific gravity of the relatively light phase and that of the heavy phase so that it forms a partition between the phases upon separation of the phases.

These as well as other objects and advantages of the present invention will become apparent from the following detailed description and accompanying drawing.

DESCRIPTION OF THE PREFERRED EMBODIMENT

Figures 1, 2, 3, 4, 5:
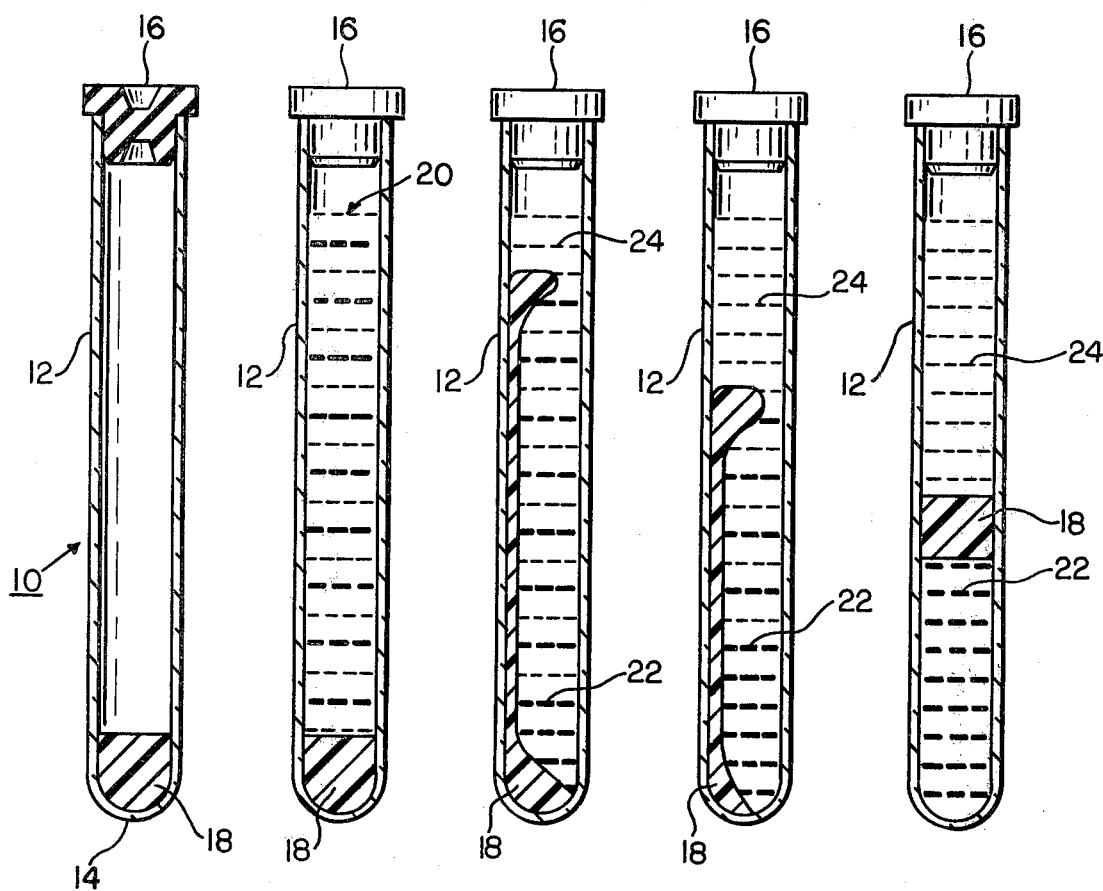
FIG. 1 is an elevational cross-sectional view of a blood collection tube containing blood phase separation material in accordance with a preferred embodiment of the present invention.
FIG. 2 is an elevational cross-sectional view of the collection tube of FIG. 1 after whole blood has been drawn into the tube.
FIG. 3 is an elevational cross-sectional view of the tube of FIG. 1 illustrating the condition of the separation material during a stage in the centrifugation of the tube.
FIG. 4 is an elevational cross-sectional view of the tube of FIG. 1 illustrating the condition of the separation material at a subsequent stage in the centrifugation of the tube.
FIG. 5 is an elevational cross-sectional view of the tube of FIG. 1 showing the phase separation material in its final position separating the light and heavy phases after centrifugation.

Referring now to FIG. 1, a blood collection device 10 is shown including a container or collection tube 12, preferably by transparent glass which is permanently closed at the bottom end such as by an integral portion 14 of the tube. The tube 12 has an upper open end closed by a closure member or stopper 16 which is pierceable by a needle cannula and self-sealing, and which may be formed, for example, of a suitable elastomeric material such as butyl rubber. The collection tube 12 is provided with a desired negative pressure or partial vacuum that is maintained by the stopper 16. Disposed within the tube 12 is phase separation or partitioning means 18 which is shown in an initial position against the bottom wall of the tube.

The phase separation means 18 is a quantity of a gel-like material or sealant, preferably hydrophobic, generally inert to the separated phases, and having a specific gravity intermediate the specific gravity of the relatively lighter phase, blood plasma or serum, and that of the heavier or cellular phase. The gel-like material 18 is flowable when subjected to centrifugal forces during centrifugation of the collection tube and automatically flows to the interface of the two phases, that is, below the light phase and above the heavy phase, to form a barrier or partition between the phases, as will be discussed more fully hereinafter.

The material 18 includes a liquid hydrocarbon-polymer, preferably liquid polybutene. Material 18 is preferably a mixture of liquid polybutene and a suitable inert filler material in such proportions that the mixture has the desired specific gravity between that of the lighter phase and that of the heavier phase, and such that it has a viscosity or consistency of a semi-solid or is substantially non-flowable at rest and under normal handling conditions of the tube such as tipping, shipping or mailing. Also, the proportions of polybutene and filler should be such that it is flowable during centrifugation of blood in the tube, and preferably at speeds of rotation normally employed to effect phase separation of the blood.

A preferred phase separation material 18 is a mixture of a liquid polybutene with a sufficient amount of silica powder filler to produce a mixture having a specific gravity between about 1.035 and 1.065, and preferably about 1.045, since the specific gravity of the lighter blood phase is between about 1.02 and 1.03 and that of the cellular phase or blood cells is between about 1.08 and 1.09.

FIG. 2 diagramatically illustrates the tube 12 after a quantity of whole blood 20 has been drawn into the tube from a patient, for example, by means of a conventional needle holder having a double-ended needle, as previously mentioned herein.

Where serum is to be separated from the whole blood, the blood filled tube 12, after a short standing period, such as 30 minutes, is placed in a centrifuge with the lower end 14 radially outwardly of the stopper 16 and axis of rotation. During centrifugation, the centrifugal forces cause the relatively heavy components including blood cells and fibrin 22 to move toward the lower end, as viewed in the drawing, with the top portion gradually becoming cell-free serum 24, as diagramatically indicated in FIGS. 3–5. The movement of the heavier blood components toward the lower end of the tube causes the separation material 18 to be displaced and to flow upwardly toward the cell-free or serum phase 24, as diagramatically seen in FIG. 3, since the specific gravity of the material 18 is less than that of the cellular phase 22. FIG. 4 shows a subsequent stage of centrifugation of the tube 12 and illustrates further separation of the two phases and the further movement of the separation material 18. The material 18 tends to stay below the serum phase since it has a greater specific gravity than the serum phase. The actual flow path of the material 18 from its initial location to its final location will vary with such factors as material composition, specific gravity, viscosity, and speed of the centrifuge.

Upon complete separation of the phases 22 and 24, as diagramatically seen in FIG. 5, the separation material 18 is disposed between the serum and cellular phases to provide a semi-solid or firm partition or seal across the interior of the tube, the seal intimately contacting and adhering to the interior surfaces of the tube to prevent any flow of fluid across the partition.

The tube 12 with its separated and partitioned serum and cellular phases, as seen in FIG. 5, may be stored or shipped to a laboratory for analysis without the danger of the cellular portion 22 or the separation means 18 contaminating the upper serum phase. When desired, the serum is easily removed from tube 12 by merely removing stopper 16 and pouring the serum from the tube 12, the substantially permanent and non-flowable partition member 18 (FIG. 5) preventing the flow of the cellular phase from the tube.

Where it is desired to obtain plasma instead of serum, a conventional anti-coagulant, such as heparin, may be inserted into the tube 12 before or after blood is introduced into the tube and, preferably, it is inserted during manufacture of the device 10 so that the stopper 16 does not have to be removed for this purpose. In such a case, the formation of a blood clot is prevented. The function of the separation material 18 will, of course, be the same as in the case of serum. In other words, the upper phase shown In FIG. 5 at 24 will be plasma instead of serum.

A highly staisfactory mixture for use as the partitioning material 18 includes 100 parts by weight of liquid polybutene, known as Polybutene Grade 24, manufactured by the Chevron Chemical Company of San Francisco, Calif.; 20 parts by weight of conventional hydrophillic silica powder ($SiO_2$) filler material, known as Min-U-Sil 10, manufactured by PGS (a subsidiary of ITT) of Pittsburgh, Pa.; and 9 parts by weight of a second silica powder known as Aerosil R-972, for Degussa Inc., Pigments Division, of New York, N.Y. The above Polybutene Grade 24 has a specific gravity of 0.898 @ 60/60° F. (ASTM D-287), and a viscosity of 40,000 SSU at 100° F. (ASTM D-445 and D-446). The Min-U-Sil 10 powder has a specific gravity of about 2.65 and with the majority of it having a particle size below 10 microns. The Aerosil R-972 silica powder is a hydrophobic silica powder having a specific gravity of about 2.2 and an average size of about $20 \times 10^{-7}$ cm. This powder was made hydrophobic by a process including flame hydrolysis of silica, and then reacting the silica with dimethyl dichlorosilane and steam into a fluidized bed reactor heated to about 400° C. by means of an inert gas such as nitrogen (publication—"Chemiker-Zeitung/Chemische Apparatur" 89 (1965), 437–440, Heidelberg/Germany). The specific gravity of the combined materials or mixture forming the separation material 18 was about 1.045 and had a viscosity or consistency such that it would not flow when the tube was tipped. The table below lists a number of other mixtures which can satisfactorily be used as separation materials:

| No. | Polybutene Grade | Polybutene gms. | Min-U-Sil 10 gms. | AEROSIL R-972 gms. |
| --- | --- | --- | --- | --- |
| 1 | Polybutene 24 | 100 | 23 | 5 |
| 2 | Polybutene 32 | 100 | 20 | 7 |
| 3 | Polybutene 24 | 100 | 18 | 12 |

While the specific gravities of the mixtures No. 1, 2 and 3 were, of course, about the same (about 1.045), the viscosity or consistency of each varied. It was found that the hydrophobic Aerosil R-972 silica powder had a greater effect on the consistency of the mixture than that of the Min-U-Sil 10 powder. The mixture was made substantially thicker for a small increase in the amount of hydrophobic silica so that the desired specific gravity and consistency was readily obtained. The Polybutene Grade 32 was similar to the Grade 24 but had a viscosity of 104,000 SSU at 100° F. Both of the Grades 24 and 32 are hydrophobic and are indicated as having a water content, (ASTM D-1533) of 40 ppm. The above-mentioned Polybutenes are described in a publication entitled "Chevron Polybutenes", 1969, by the Chevron Chemical Company.

The use of the relatively smaller amount of hydrophobic silica powder in each of the separation mixtures described herein apparently also has the effect of preventing separation of the silica from the polybutene. In using the described mixtures, there appeared to be substantially no migration of silica into the separated phases, or during subsequent handling or shipping. Thus, the separation partition 18 provides a firm, permanent barrier between the separated phases allowing them to remain in the same tube without interaction and during subsequent handling.

While the use of hydrophobic silica powder in the separation mixture 18 is preferred, it has been found that liquid polybutene and a filler entirely of hydrophillic silica powders is useful in some cases as an especially economical partition barrier since silica powder is less expensive than the hydrophobic silica powder. For example, where centrifugation is stopped relatively soon after complete separation of the phases has occurred and the lighter phase is decantered soon after centrifugation, the latter type of partition material may be satisfactorily used.

The axial length of the partition 18, as viewed in FIG. 5, is not critical. While a length of about one-half inch has been satisfactory, greater or lesser lengths may be employed.

While liquid polybutene has been found to provide good results, other organic liquid polymers or hydrocarbon-polymers such as liquid butyl rubber and liquid polybutadiene are believed to also be suitable for use in providing a centrifugally actuated partitioning material 18. For example, such hydrocarbon-polymers may be mixed with silica powders such as the above-mentioned powders and in such proportions as to provide a desired specific gravity between the specific gravities of the two phases of blood and such that they flow during centrifugation to form a substantially hydrophobic, non-flowable barrier seal between the phases after centrifugation and when subjected to normal handling, for example, when mailed.

It was found that when employing a separation mixture 18 formed of polybutene, substantially no oily film or droplets were produced that clog tubing in test equipment, as was the case with silicone gels. Also, the low molecular weight polybutene liquid is substantially less costly than silicone fluids.

Since a blood clot will readily flow by the flowable mixture 18 during centrifuging, an economical collection tube 12, having an integrally closed bottom end such as indicated at 14 in the drawing, may be used for serum separation as well as plasma separation, thus avoiding the necessity of a more expensive double-stopper tube for serum separation.

While the phase partitioning or separation material 18 can be used as the only phase separation means as shown and described herein, an additional member or members, such as a plastic member having a specific gravity intermediate those of the two phases, may be used in conjunction with separation material where desired. For example, in the device shown in FIGS. 6 and 7 of the previously mentioned U.S. Pat. No. 3,852,194, a spool member having a central opening and which may be of rubber, cooperates with gel-like material in forming a barrier.

While gel-like material 18 of the present invention can be advantageously used in a tube having only one end that can be opened or has only one stopper, such as tube 12, it can also be advantageously used in a container or tube of the type having opposed ends closed by stoppers. For example, the gel-like material 18 may be used in tubes of the type described in U.S. Pat. 3,782,197. This patent discloses a device for discharging fluid from a tube without requiring the removal of a stopper from either end. In this patent, after a needle that is connected to tubing pierces the stopper at one end of the tube, a rod moves the second stopper at the opposite end further into the tube forcing fluid into the needle and tubing.

Filler materials other than silica powders may also be used in forming the gel-like material 18. For example, powders such as talc, bentonite, celite, plastics such as fluorocarbon polymers, or the like, may be useful in serving as a filler or a portion of a filler in the gel material.

Also, blood clotting materials, anticoagulant materials, or other materials which are desired to be disposed in the blood specimen may be disposed in the collection device during or after manufacture.

As various changes could be made in the above construction without departing from the scope of the invention, it is intended that all matter contained in the above description or shown in the accompanying drawing shall be interpreted as illustrative and not in a limiting sense.

What is claimed is:

1. A fluid collection device comprising:
(1) a container for receiving a specimen of a fluid separable into relatively lighter and heavier phases under centrifugation; and,
(2) a phase separation means in said container comprising:
  (a) a gel-like material having a specific gravity intermediate the specific gravities of the separate phases
  (b) said gel-like material being flowable from an initial position when said container with the fluid therein is subjected to centrifugation to a final position between the separate phases to form a substantially non-flowable partition between the separate phases, (c) said gel-like material being such that it does not substantially contaminate the separated lighter phase,
(d) said gel-like material comprising a mixture of polybutene and a powdered filler with the mixture having a specific gravity ranging from 1.035 to 1.065.

2. The device of claim 1 wherein said filler is a powder substantially inert with respect to the lighter phase.

3. The device of claim 2 wherein said filler comprises an inorganic powder.

4. The device of claim 3 wherein said inorganic powder is a silica powder.

5. The device of claim 3 wherein said filler comprises hydrophillic silica powder and hydrophobic silica powder.

6. The device of claim 3 wherein said filler comprises essentially only hydrophillic silica powder.

7. The device of claim 1 wherein said container has a closed end and an open end, a stopper extending into said open end to sealingly close the interior of said container and said material from the atmosphere, said stopper being pierceable by a needle cannula for introducing the specimen of fluid into said container.

8. The device of claim 7 wherein said container has a negative pressure therein prior to receiving the specimen of fluid.

9. The device of claim 8 wherein said phase separation means is adjacent said closed end of said container before said container receives the specimen of fluid.

10. The device of claim 8 wherein said closed end of said container is closed by an integral portion of said container.

11. The device of claim 1 wherein said phase separation means consists of only said gel-like material which constitutes the only means for partitioning the phases.

12. A fluid collection device comprising:
(1) a container for receiving a specimen of a fluid separable into relatively lighter and heavier phases under centrifugation; and,
(2) a phase separation means in said container comprising:
  (a) a gel-like material having a specific gravity intermediate the specific gravities of the separate phases,
  (b) said gel-like material being flowable from an initial position when said container with the fluid therein is subjected to centrifugation to a final position between the separate phases to form a substantially non-flowable partition between the separate phases,
  (c) said gel-like material being such that it does not substantially contaminate the separated lighter phase,
  (d) said gel-like material comprising a mixture of liquid butyl rubber and a powdered filler with the mixture having a specific gravity ranging from 1.035 to 1.065.

13. A fluid collection device comprising:
(1) a container for receiving a specimen of a fluid separable into relatively lighter and heavier phases under centrifugation; and,
(2) a phase separation means in said container comprising:
  (a) a gel-like material having a specific gravity intermediate the specific gravities of the separate phases,
  (b) said gel-like material being flowable from an initial position when said container with the fluid therein is subjected to centrifugation to a final position between the separate phases to form a substantially non-flowable partition between the separate phases,
  (c) said gel-like material being such that it does not substantially contaminate the separated lighter phase,
  (d) said gel-like material comprising a mixture of liquid polybutadiene and a powdered filler with the mixture having a specific gravity ranging from 1.035 to 1.065.

14. A blood collection device comprising:
(1) a tube for receiving a sample of blood adapted to be centrifically separated into relatively lighter and heavier phases while in said tube,
(2) means closing one end of said tube,
(3) a stopper sealingly closing the opposite end of said tube,
(4) a negative pressure in said tube and maintained by said stopper,
(5) blood phase partitioning means disposed in said tube,
(6) said stopper being pierceable by a needle for drawing whole blood into said tube for centrifugation with said partitioning means,
(7) said partitioning means comprising a gel-like material having a specific gravity between that of the lighter phase of blood and that of the heavier phase of blood and being flowable during centrifugation of the blood from an initial position in said tube to a position between said phases upon separation of said phases,
(8) said material being substantially non-flowable after separation of said phases under normal handling conditions to form a barrier contact in the inner walls of said tube to sealingly separate said phases from each other,
(9) said gel-like material being such that it does not substantially contaminate the separated lighter phase, and
(10) the gel-like material comprising a mixture of polybutene and a powder filler with the mixture having a specific gravity ranging from about 1.035 to 1.065.

15. The device of claim 14 wherein said filler material comprises silica powder.

16. The device of claim 14 wherein at least some of said filler includes hydrophobic silica powder.

17. The device of claim 16 wherein said filler further includes hydrophillic silica powder.

18. The device of claim 14 wherein said partitioning means consists of only said gel-like material.

19. A blood collection device comprising:
(1) a tube for receiving a sample of blood adapted to be centrifugally separated into relatively lighter and heavier phases while in said tube,
(2) means closing one end of said tube,
(3) a stopper sealingly closing the opposite end of said tube,
(4) a negative pressure in said tube and maintained by said stopper,
(5) blood phase partitioning means disposed in said tube,
(6) said stopper being pierceable by a needle for drawing whole blood into said tube for centrifugation with said partitioning means,
(7) said partitioning means comprising a gel-like material having a specific gravity between that of the lighter phase of blood and that of the heavier phase of blood and being flowable during centrifugation of the blood from an initial position in said tube to a position between said phases upon separation of said phases, (8) said material being substantially non-flowable after separation of said phases under normal handling conditions to form a barrier contact in the inner walls of said tube to sealingly separate said phases from each other, (9) said gel-like material being such that it does not substantially contaminate the separated lighter phase, and

(10) the gel-like material comprising a mixture of liquid polybutadiene and a powder filler with the mixture having a specific gravity ranging from about 1.035 to 1.065.

* * * * *

UNITED STATES PATENT AND TRADEMARK OFFICE
CERTIFICATE OF CORRECTION

PATENT NO. : 4,180,465
DATED : December 25, 1979
INVENTOR(S) : Vabilisetti S. Murty It is certified that error appears in the above—identified patent and that said Letters Patent is hereby corrected as shown below:

The term of this patent subsequent to May 3, 1994 has been disclaimed.

Signed and Sealed this

Twenty-sixth Day of February 1980

[SEAL]

*Attest:*

SIDNEY A. DIAMOND

*Attesting Officer*  *Commissioner of Patents and Trademarks*